United States Patent
Wang et al.

(10) Patent No.: US 7,591,816 B2
(45) Date of Patent: Sep. 22, 2009

(54) IRRIGATED ABLATION CATHETER HAVING A PRESSURE SENSOR TO DETECT TISSUE CONTACT

(75) Inventors: Huisun Wang, Maple Grove, MN (US); Hong Cao, Savage, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 223 days.

(21) Appl. No.: 11/646,270

(22) Filed: Dec. 28, 2006

(65) Prior Publication Data
US 2008/0161794 A1     Jul. 3, 2008

(51) Int. Cl.
*A61B 18/14* (2006.01)
(52) U.S. Cl. .......................................... 606/41
(58) Field of Classification Search ............. 606/32–52; 600/403, 404
See application file for complete search history.

(56) References Cited

U.S. PATENT DOCUMENTS

| | | | |
|---|---|---|---|
| 5,056,517 A | 10/1991 | Fenici | |
| 5,230,349 A | 7/1993 | Langberg | |
| 5,348,554 A | 9/1994 | Imran et al. | |
| 5,423,811 A | 6/1995 | Imran et al. | |
| 5,427,114 A * | 6/1995 | Colliver et al. | 600/561 |
| 5,462,521 A | 10/1995 | Brucker et al. | |
| 5,545,161 A | 8/1996 | Imran | |
| 5,643,197 A | 7/1997 | Brucker et al. | |
| 5,697,927 A | 12/1997 | Imran | |
| 5,792,140 A | 8/1998 | Tu et al. | |
| 5,843,152 A | 12/1998 | Tu et al. | |
| 5,913,856 A | 6/1999 | Chia et al. | |
| 6,017,338 A | 1/2000 | Brucker et al. | |
| 6,602,242 B1 | 8/2003 | Fung et al. | |
| 6,611,699 B2 | 8/2003 | Messing | |
| 6,659,959 B2 * | 12/2003 | Brockway et al. | 600/488 |
| 6,955,675 B2 * | 10/2005 | Jain | 606/41 |
| 7,166,105 B2 | 1/2007 | Mulier et al. | |
| 2005/0256521 A1 | 11/2005 | Kozel | |
| 2006/0036303 A1 | 2/2006 | Schwartz | |
| 2006/0058854 A1 | 3/2006 | Abrams | |
| 2006/0278248 A1 | 12/2006 | Viswanathan | |

FOREIGN PATENT DOCUMENTS

WO    WO 2005/048858 A1    6/2005

OTHER PUBLICATIONS

International Searching Authority; PCT/US07/88192; International Search Report dated Jun. 13, 2008.
International Searching Authority; PCT/US07/88192; Written Opinion dated Jun. 13, 2008.
Wittkampf, et al., "Radiofrequency Ablation With a Cooled Porous Electrode Catheter," JACC vol. 11, No. 2, Feb. 1988: 17A Abstracts.
Wittkampf, et al., "Saline-Irrigated Radiofrequency Ablation Electrode with External Cooling," Journal of Cardiovascular Electrophysiology, vol. 16, No. 3, Mar. 2005.

* cited by examiner

*Primary Examiner*—Michael Peffley
*Assistant Examiner*—Ronald J Hupczey, Jr.
(74) *Attorney, Agent, or Firm*—Dykema Gossett LLP

(57) ABSTRACT

The invention relates to an irrigated ablation catheter that has a pressure sensor to determine tissue contact as well as methods of using the same. The irrigated ablation catheter contains fluid tubing, an electrode with passages and a lumen and a pressure sensor located inside the lumen of the electrode. In some embodiments, a cooling fluid, such as saline, is passed through the catheter.

32 Claims, 5 Drawing Sheets

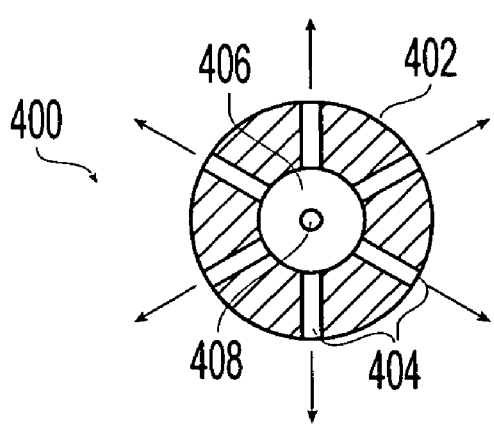 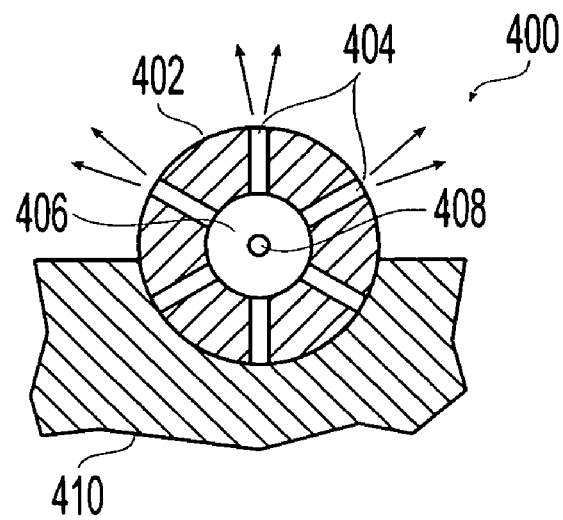
*Fig. 4a*  *Fig. 4b*

IRRIGATED ABLATION CATHETER HAVING A PRESSURE SENSOR TO DETECT TISSUE CONTACT

CROSS-REFERENCE TO RELATED APPLICATIONS

This application is related to U.S. application Ser. No. 11/646,275, filed Dec. 28, 2006 and entitled Irrigated Ablation Catheter System With Pulsatile Flow To Prevent Thrombus, now pending; U.S. application Ser. No. 11/646,237, filed Dec. 28, 2006 and entitled Irrigated Ablation Catheter Having A Valve To Prevent Backflow, now pending; and U.S. application Ser. No. 11/646,255, filed Dec. 28, 2006 and entitled Cooled Ablation Catheter With Reciprocating Flow, now pending. These applications are all hereby incorporated by reference in their entirety as though fully set forth herein.

BACKGROUND OF THE INVENTION a. Field of the Invention

The instant invention relates to ablation catheters. In particular, the instant invention relates to an irrigated ablation catheter that has an internal pressure sensor to detect tissue contact and methods of operating the catheter.

b. Background Art

Electrical stimulation of myocardial tissue controls the pumping action of the heart. Stimulation of this tissue in various regions of the heart is controlled by a series of conduction pathways contained within the myocardial tissue. In a healthy heart, contraction and relaxation of the heart muscle (myocardium) occur in an organized fashion as electrochemical signals pass sequentially through the myocardium from the sinoatrial (SA) node, which consist of a bundle of unique cells disposed in the wall of the right atrium, to the atrioventricular (AV) node, and then into the left and right ventricles via a route that includes the His-Purkinje system. The AV node is located near the ostium of the coronary sinus in the interatrial septum in the right atrium. Each cell membrane of the SA node has a characteristic tendency of a gradual leak of sodium ions over time leading to a periodic break down of the cell membrane, thus allowing an inflow of sodium ions, and thereby causing the SA node cells to depolarize. The SA node cells are in communication with the surrounding atrial muscle cells such that the depolarization of the SA node cells causes the adjacent atrial muscle cells to also depolarize. This depolarization results in atrial systole, during which the atria contract to empty and fill blood into the ventricles. The AV node detects the atrial depolarization from the SA node and, in turn, relays the depolarization impulse into the ventricles via the bundle of His and Purkinje fibers following a brief conduction delay. The His-Purkinje system begins at the AV node and follows along the membranous interatrial septum toward the tricuspid valve through the AV septum and into the membranous interventricular septum. At about the middle of the interventricular septum, the His-Purkinje system splits into right and left branches, which straddle the summit of the muscular part of the interventricular septum.

Abnormal rhythms generally referred to as arrhythmia can occur in the heart. Cardiac arrhythmias arise when the pattern of the heartbeat is changed by abnormal impulse initiation or conduction in the myocardial tissue. The term tachycardia is used to describe an excessively rapid heartbeat resulting from repetitive stimulation of the heart muscle. Such disturbances often arise from additional conduction pathways that are present within the heart either from a congenital developmental abnormality or an acquired abnormality, which changes the structure of the cardiac tissue, such as a myocardial infarction.

A common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle.

Atrial arrhythmia may also occur. Three of the most common atrial arrhythmia are ectopic atrial tachycardia, atrial fibrillation, and atrial flutter. Atrial fibrillation can cause significant patient discomfort and even death because of a number of associated problems, including e.g., an irregular heart rate (which causes patient discomfort and anxiety), loss of synchronous atrioventricular contractions (which compromises cardiac hemodynamics, resulting in varying levels of congestive heart failure) and stasis of blood flow (which increases the likelihood of thromboembolism).

In the past, problems associated with arrhythmia have been treated with pharmacological treatment. Such treatment may not be effective in all patients and is frequently plagued with side effects, including, e.g., dizziness, nausea, vision problems, and other difficulties.

Alternatively, such disturbances are treated by identifying the conductive pathways and then severing part of this pathway by destroying these cells, which make up a portion of the pathway. Traditionally, this has been done by either cutting the pathway surgically; freezing the tissue, thus destroying the cellular membranes; or by heating the cells, thus denaturing the cellular proteins. The resulting destruction of the cells eliminates their electrical conductivity, thus destroying, or ablating, a certain portion of the pathway. By eliminating a portion of the pathway, the pathway may no longer maintain the ability to conduct, and the tachycardia ceases.

Catheters are a common medical tool that has been used for many years. They are employed, e.g., for medical procedures to examine, diagnose, and treat while positioned at a specific location within the body that is otherwise inaccessible without more invasive procedures. In such procedures, a catheter is first inserted into a vessel near the surface of the body and the guided to a specific location within the body. For example, a catheter may be used to convey an electrical stimulus to a selected location within the human body or a catheter with sensing electrodes may be used to monitor various forms of electrical activity in the human body.

Catheters have increasingly become a common medical procedure for the treatment of certain types of cardiac arrhythmia. Catheter ablation is based on the idea that by ablation (i.e., destroying) abnormal tissue areas in the heart, its electrical system can be repaired and the heart will return to a normal rhythm. During catheter ablation, the catheter is typically inserted in an artery or vein in the leg, neck, or arm of the patient and then threaded, sometimes with the aid of a guide wire or introducer, through the vessels until a distal tip of the catheter reaches the desired location for the medical procedure in the heart.

Most often, cardiac ablation is used to treat supraventricular tachycardias, or SVTs. Types of SVTs are atrial fibrillation, atrial flutter, AV nodal reentrant tachycardia, AV reentrant tachycardia, and atrial tachycardia. Less frequently, ablation can treat heart rhythm disorders that begin in the heart's lower chambers, known as the ventricles. The most common, ventricular tachycardia may also be the most dangerous type of arrhythmia because it can cause sudden cardiac death. For patients at risk for sudden cardiac death, ablation often is used along with an implantable cardioverter device (ICD). The ablation decreases the frequency of abnormal heart rhythms in the ventricles and therefore reduces the number of ICD shocks a patient may experience. For many types of arrhythmias, catheter ablation is successful in 90-98 percent of cases, thus eliminating the need for open-heart surgeries or long-term drug therapies.

During conventional catheter ablation procedures, an energy source is in contact with cardiac tissue to heat the tissue and create a permanent scar or lesion that is electrically inactive or non-contractile. These lesions are designed to interrupt existing conduction pathways commonly associated with arrhythmias within the heart. The particular area for ablation depends on the type of underlying arrhythmia. One common ablation procedure treats atrioventricular nodal reentrant tachycardia (AVNRT). The use of electrode catheters for ablating specific locations within the heart has also been disclosed in, e.g., U.S. Pat. Nos. 4,641,649, 5,228,442, 5,231,995, 5,263,493, and 5,281,217.

Many variations of ablations procedures are known. For example, ablation of fast or slow AV nodal pathways is disclosed in Singer et al., Catheter Ablation for Arrhythmias, Clinical Manual of Electrophysiology, 421-431 (1993).

Another medical procedure using ablation catheters with sheaths to ablate accessory pathways associated with W-P-W using both a transseptal and retrograde approach is discussed in Saul et al., Catheter Ablation of Accessory Atrioventricular Pathways in Young Patients: Use of long vascular sheaths, the transseptal approach and a retrograde left posterior parallel approach, Journal of the American College of Cardiology, 21, 571-583 (1993). Additional catheter ablation procedures are disclosed in Swartz, Radiofrequency Endocardial Catheter Ablation of Accessory Atrioventricular Pathway Atrial Insertion Sites, Circulation, 87, 487-499 (1993).

Ablation of a specific target requires precise placement of the ablation catheter within the heart. Precise positioning of the ablation catheter is especially difficult due the physiology of the heart, particularly since the heart continues to beat throughout the ablation procedures. Typically, the choice of placement of the catheter is determined by a combination of electrophysiological guidance and fluoroscopy. Fluoroscopy is placement of the catheter in relation to known features of the heart, which are marked by radiopaque diagnostic catheters that are placed in or at known anatomical structures, such as the coronary sinus, high right atrium, and the right ventricle.

Ablation procedures using guiding introducers to direct an ablation catheter to a particular location in the heart for treatment of atrial arrhythmia have been disclosed in, e.g., U.S. Pat. Nos. 5,427,119, 5,497,774, 5,564,440, 5,575,766, 5,628,316, and 5,640,955. During these procedures, ablation lesions are produced in the heart.

A variety of energy sources can be used to supply the energy necessary to ablate cardiac tissue and create a permanent lesion. Such energy sources include direct current, laser, microwave, and ultrasound. Because of problems associated with the use of DC current, radiofrequency (RF) has become the preferred source of energy for ablation procedures. The use of RF energy for ablation has been disclosed, e.g., in U.S. Pat. Nos. 4,945,912, 5,242,441, 5,246,438, 5,281,213, 5,281,218, and 5,293,868. The use of RF energy with an ablation catheter contained within a transseptal sheath for the treatment of W-P-W in the left atrium is disclosed in Swartz et al., Radiofrequency Endocardial Catheter Ablation of Accessory Atrioventricular Pathway Atrial Insertion Sites, Circulation, 87: 487-499 (1993). See also Tracey, Radio Frequency Catheter Ablation of Ectopic Atrial Tachycardia Using Paced Activation Sequence Mapping, J. Am. Coll. Cardiol. 21: 910-917 (1993).

In addition to radiofrequency ablation catheters, thermal ablation catheters are also used. During thermal ablation, a heating element, secured to the distal end of a catheter, heats thermally conductive fluid. This fluid then contacts the human tissue to raise its temperature for a sufficient period of time to ablate the tissue. A method and device for thermal ablation using heat transfer is disclosed in U.S. Pat. No. 5,433,708. U.S. Pat. No. 5,505,730 discloses another thermal ablation procedure. This procedure utilizes a thermal electrode secured to a catheter and located within a balloon with openings in that balloon. The openings permit a heated conductive fluid introduced into the balloon from the catheter to escape to contact the tissue to be ablated.

Conventional ablation procedures use a single electrode secured to the tip of an ablation catheter. It has become increasingly more common to use multiple electrodes affixed to the catheter body. Such ablation catheters often contain a distal tip electrode and a plurality of ring electrodes as disclosed in, e.g., U.S. Pat. Nos. 4,892,102, 5,228,442, 5,327,905, 5,354,297, 5,487,385, and 5,582,609.

During conventional ablation procedures, the ablating energy is delivered directly to the cardiac tissue by an electrode on the catheter placed against the surface of the tissue to raise the temperature of the tissue to be ablated. The increase in tissue temperature also results in a rise in the temperature of blood surrounding the electrode. This rise in temperature often results in the formation of coagulum on the electrode, which in turn reduces the efficiency of the ablation electrode. Thus, to achieve efficient and effective ablation, coagulation of blood should be avoided. This coagulation problem can be especially significant when linear ablation lesions or tracks are produced because such linear ablation procedures take more time than ablation at only a single location.

The formation of linear lesions within a heart via conventional ablation tip electrode requires use of procedures such as e.g., a "drag burn." A "linear lesion" means an elongate, continuous lesion, which may be straight or curved, that blocks electrical conduction. During a "drag burn" procedure, while energy is supplied to the electrode, the electrode is drawn across the tissue to be ablated, producing a line of ablation. Alternatively, a series of points of ablation are formed in a line created by moving the tip electrode incremental distances across the cardiac tissue. The effectiveness of these procedures depends on a number of variables such as e.g., (i) the position and contact pressure of the tip electrode of the ablation catheter against the cardiac tissue, (ii) the time that the tip electrode of the ablation catheter is placed against the tissue, (iii) the amount of coagulum formed as a result of heat generated during the ablation procedure, and (iv) other variables associated with a beating heart, especially an erratically beating heart. An uninterrupted track of cardiac tissue needs to be ablated as unablated tissue or incompletely ablated tissue may remain electrically active, thereby permitting the continuation of stray circuits that cause arrhythmia.

More efficient ablation can be achieved if a linear lesion of cardiac tissue is formed during a single ablation procedure. The production of linear lesions in the heart by use of an ablation catheter is disclosed in, e.g., U.S. Pat. Nos. 5,487,385, 5,582,609, and 5,676,662. A specific series of linear lesions formed in the atria for the treatment of atrial arrhythmia are disclosed in U.S. Pat. No. 5,575,766.

Physical contact of the cardiac tissue with an electrode of the ablation catheter is typically used to perform these procedures on electrically inactive or non-contractile tissue.

Conventional tip electrodes with adjacent ring electrodes cannot perform this type of procedure, however, due to the high amount of energy necessary to ablate sufficient tissue to produce a complete linear lesion. In addition, conventional ring electrode ablation may leave holes or gaps in a lesion, which can provide a doorway for the creation of unwanted circuits.

U.S. Pat. No. 5,334,193 discloses an ablation catheter for use in the heart that contains a pair of intertwined helical electrodes. The helically wound electrode is affixed to the surface of the catheter body over a distance of about eight centimeters from the distal tip of the catheter body. Other helical electrodes are disclosed in WO 95/10319 as well as U.S. Pat. Nos. 4,161,952, 4,776,334, 4,860,769, 4,934,049, 5,047,026, and 5,542,928.

As discussed a variety of energy such as radiofrequency (RF), microwave, ultrasound, and laser energy have been used for ablation. With RF energy, a catheter with a conductive inner core and a metallic tip are placed in contact with the myocardium and a circuit is completed with a patch placed on the patient's body behind the heart. The catheter is coupled to a RF generator such that application of electrical energy creates localized heating in the tissue adjacent to the distal (emitting) electrode. The peak tissue temperatures during catheter delivered application of RF energy to the myocardium occur close to the endocardial surface, such that the lesion size produced is limited by the thermodynamics of radiant heat spread from the tip. The amount of heating which occurs is dependent on the area of contact between the electrode, and the tissue and the impedance between the electrode and the tissue. The higher the impedance, the lower the amount of energy transferred into the tissue.

During RF catheter ablation, local temperature elevation can result in coagulum formation on the ablation electrode, resulting in impedance rise. As the impedance increases, more energy is passed through the portion of the tip without coagulation, creating even higher local temperatures and further increasing coagulum formation and the impedance. Finally, enough blood coagulates onto the tip that no energy passes into the tissue. The catheter must now be removed from the vascular system, the tip area cleaned and the catheter repositioned within the heart at the desired location. Not only can this process be time consuming, but also it may be difficult to return to the previous location because of the reduced electrical activity in the regions, which have previously been ablated. A recent study has also demonstrated the formation of a so-called soft thrombus during experimental ablations (Demonlin et al. Soft thrombus formation in radiofrequency catheter ablation, Pacing clin. electrophysiol. 25: 1219-1222 (2002)). The formation of the so-called soft thrombus results from heat induced protein denaturation and aggregation and occurs independent of heparin concentration in serum.

To prevent the occurrence of, e.g., soft thrombus, blood coagulation, and steam pop during ablation, the catheter may be cooled by passing a fluid through the catheter during ablation. Saline irrigation is an effective way to cool the ablation electrode and keep efficient flow around the electrode to prevent blood coagulation. Furthermore, the surface cooling that results from the saline irrigation reduces heating at the point of highest current density where excessive temperatures would normally produce charring, crater formation and impedance rises (Thomas et al., A comparison of open irrigated and non-irrigated tip catheter ablation for pulmonary vein isolation, Europace 6: 330-335 (2004)). Open irrigated ablation catheters are currently the most common irrigated catheters in the electrophysiology field. Examples of these devices include Thermocool® by Biosense Webster and Coolpath® by Irvine Biomedical.

It is also important to ensure that the appropriate amount of energy necessary to destroy the tissue is delivered. In an RF ablation catheter, this is achieved by maintaining a good contact between the target tissue and electrode. A number to technologies have been developed to detect the contact between the target tissue and electrode. Most of these methods rely on deflection of the catheter to detect catheter contacting.

There remains a need to detect contact between the catheter and target tissue without bending of the catheter.

BRIEF SUMMARY OF THE INVENTION

It is desirable to be able to provide an irrigated ablation catheter that detects contacting between the target tissue and catheter without relying on catheter deflection.

One embodiment of the invention is an irrigated ablation catheter with a pressure sensor mounted in the catheter. The irrigated ablation catheter may utilize radiofrequency energy to ablate the target tissue. The irrigated ablation catheter may also be packaged as part of a kit.

The irrigated ablation catheter includes an elongated tubing having a distal end, a proximal end, and a lumen. The irrigated ablation catheter also has an electrode attached to the distal end of the tubing. The electrode has an inner cavity, a plurality of passages from the inner cavity to an outer surface of the electrode as well as a distal end and a proximal end. The catheter also has a shaft with a distal end and a proximal end. The distal end of the shaft is attached to the proximal end of electrode and external to the tubing. The catheter also includes a pressure sensor located inside the inner cavity of the electrode.

The electrode may be made of platinum (Pt), iridium (Ir), gold, a gold alloy, a noble metal, or stainless steel. In one embodiment, the electrode is made from a Pt and Ir alloy. The pressure sensor may be a fiber optic sensor, which may be connected to a fiber optic cable. The tubing is flexible. The total area of the passages in the electrode may be smaller than the cross-sectional area of the lumen of the tubing. The shaft may be tubular and the tubing may contain radiopaque markers or radiopaque filler. A cooling fluid, such as, e.g., saline, may be passed through the catheter.

Another embodiment of the invention is an irrigated ablation catheter encompassing an elongated tubing connected to a manifold, which in turn is connected to an electrode, a shaft connected to the manifold and a pressure sensor. The irrigated ablation catheter may use RF energy.

The elongated tubing has a distal end, a proximal end, and a lumen. The manifold has a distal end, a proximal end and a lumen, and at least one passage from the lumen to an outer surface of the manifold. The manifold is attached to the proximal end of the flexible tubing such that the lumen of the manifold and the lumen of the tubing are connected. The electrode has an inner cavity, at least one passage from the inner cavity to an outer surface of the electrode, a distal end, and a proximal end. The electrode attached to the proximal end of the manifold such that the lumen of the manifold is mated to the inner cavity of the electrode. The shaft has a distal end and a proximal end. The distal end of the shaft is attached to the proximal end of the manifold and external to the flexible tubing. The shaft may be tubular. The pressure sensor is located inside the inner cavity of the electrode.

The electrode may contain Pt, Ir, gold, a gold alloy, a noble metal, stainless steel or a Pt and Ir alloy. The pressure sensor may be a fiber optic pressure sensor, which may be connected to a fiber optic cable. In one embodiment, the total area of the passages is smaller than the cross-sectional area of the lumen of the flexible tubing. The tubing may contain radiopaque markers or radiopaque filler. A cooling fluid, such as e.g., saline, may be passed through the catheter.

The invention also encompasses methods of using irrigated ablation catheters. In one embodiment, the method of ablation has the steps of:

(a) providing an open irrigated ablation catheter comprising an electrode having a lumen and plurality of passages ways and a pressure sensor inside the lumen of the electrode;

(b) inserting the catheter into a patient;

(c) measuring the pressure in the catheter inside the patient;

(d) contacting a target tissue, (e) determining if contacting of the target tissue has been made by (i) measuring the pressure inside the catheter inside the patient after tentative target tissue contact; and (ii) comparing this pressure with that in step (c), wherein an increase in the pressure is indicative of tissue contacting; and (f) ablating the target tissue.

This method may be used when the catheter has a manifold that is mounted to the electrode, when the electrode of the catheter is Pt, Ir, or alloy thereof, when the pressure sensor of the electrode is a fiber optic pressure sensor and when a cooling fluid, such as e.g., saline, is passed through the catheter. The step of ablating may employ radiofrequency energy.

Another embodiment of the invention is an ablation catheter that has (a) elongated tubing having a distal end, a proximal end, and a lumen, (b) a shaft having a distal end, a proximal end, and a lumen, the shaft being external to the elongated tubing; (c) a distal member coupled to the distal end of the shaft to form an interior space of the catheter, the distal member having at least one passage fluidicly coupled between the interior space of the catheter and the outer surface of the distal member, the interior space of the catheter being fluidicly coupled to the lumen of the elongated tubing, the distal member including an electrode, and (d) a pressure sensor disposed inside the interior space of the catheter.

In such a catheter, the electrode may include at least one passage fluidicly coupled between the interior space of the catheter and the outer surface of the distal member. Furthermore, the distal member may include a manifold having a proximal end connected to the distal end of the shaft and a distal end connected to the electrode. This manifold may have at least one passage fluidicly coupled between the interior space of the catheter and the outer surface of the distal member. Additionally, the manifold may be made of a thermally insulative material. In one embodiment of such an ablation catheter, the electrode includes at least one passage fluidicly coupled between the interior space of the catheter and the outer surface of the distal member, and the manifold includes at least one passage fluidicly coupled between the interior space of the catheter and the outer surface of the distal member. The distal member may include an inner cavity forming a portion of the interior space of the catheter, and the pressure sensor may be disposed inside the inner cavity of the distal member.

The foregoing and other aspects, features, details, utilities, and advantages of the present invention will be apparent from reading the following description and claims, and from reviewing the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIG. 1 shows the cross-section of the electrode at the distal end of an ablation catheter with a pressure sensor located inside the lumen of the electrode.

FIG. 2 shows the cross-section of the electrode and manifold at the distal end of an ablation catheter with a pressure sensor located inside the lumen of the electrode.

FIG. 3 is a side view of the flow and pressure change inside the distal end of an irrigated catheter according to one embodiment of the invention at a perpendicular position as a result of tissue contacting.

FIG. 4 is an axial view at horizontal orientation of the flow and pressure change inside distal the irrigated catheter according to one embodiment of the invention because of tissue contacting. FIG. 4A shows the flow when there is no contacting with the target tissue. FIG. 4B shows the flow when there is contacting.

FIG. 5 is a side view at horizontal orientation of the flow and pressure change inside the distal end of an irrigated catheter according to one embodiment of the invention as a result of tissue contacting.

DETAILED DESCRIPTION OF THE INVENTION

Figure 1:
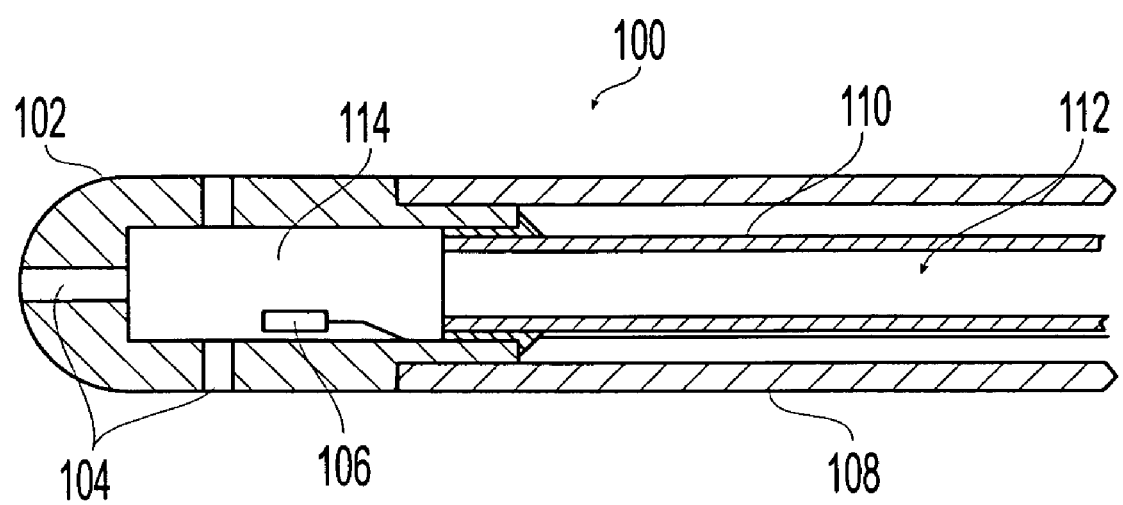
FIG. 1 is a cross-sectional view of one embodiment of an irrigated ablation catheter according to the instant disclosure.
Figure 2:
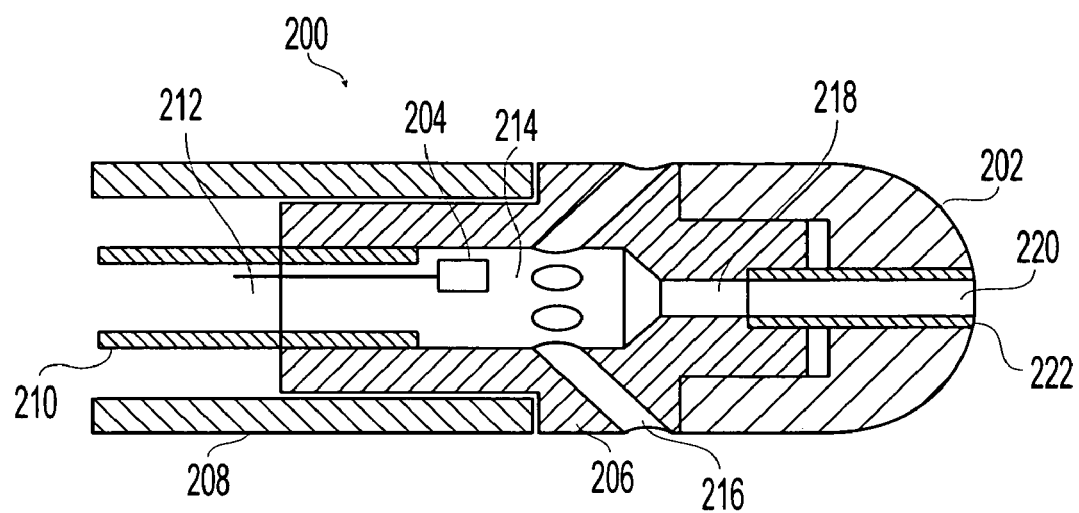
FIG. 2 is a cross-sectional view of another embodiment of an irrigated ablation catheter according to the instant disclosure.
Figure 5A:
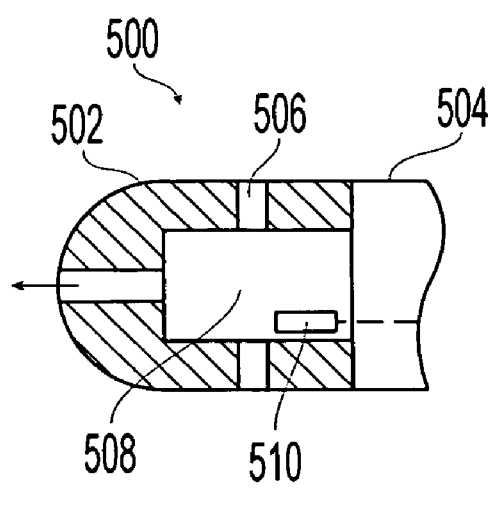
FIG. 5A show the flows when there is no contacting with the target tissue.
Figure 5B:
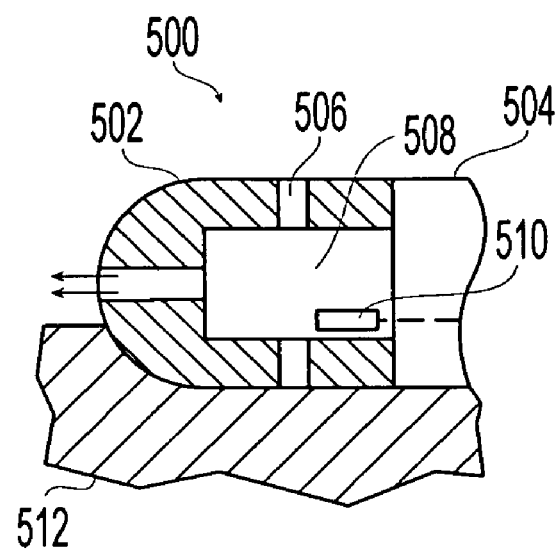
FIG. 5B shows the flow when there is contacting.

Reference will now be made in detail to the certain embodiments of the present invention, examples of which are illustrated in the accompanying drawings. FIGS. 1 and 2 show different embodiments of an irrigated ablation catheter according to the instant disclosure. As described below, the FIGS. 3 to 5 illustrate the flow and pressure change inside an irrigated ablation catheter according to the instant disclosure.

As used herein, "proximal" refers to the direction away from the body of a patient and towards a clinician. Furthermore, as used herein "distal" refers to the direction toward the body of a patient and away from the clinician.

One embodiment of the invention is an irrigated ablation catheter that utilizes an electrode with a plurality of passageways and a pressure sensor inside the electrode. Referring to FIG. 1, side elevational view of catheter 100 is shown. Catheter 100 has elongated flexible tubing 110, pressure sensor 106, shaft 108, and electrode 102. The elongated flexible tubing 110 has a distal end, a proximal end, and a lumen 112. The electrode 102 has an inner cavity 114, a plurality of passages 104 from the inner cavity to an outer surface of the electrode, as well as a distal end and a proximal end. The electrode 102 is attached to flexible tubing 110 such that the inner cavity 114 of electrode 102 is connected to the lumen 112 of the flexible tubing 110. Pressure sensor 106 is located inside the inner cavity 114.

Catheter 100 may be of varying lengths, the length being determined by the application for the catheter.

Electrode 102 may be made of any electro-conductive material suitable for medical use. Electrode 102 may be a single electrode or multiple electrodes. The electrode may contain gold, a gold alloy, a noble metal, stainless steel, platinum, and/or iridium. The electrode may contain a platinum-iridium alloy. In one embodiment of the invention, the electrode is made from a platinum-iridium alloy. The length of the electrode may be at least 4 mm alternatively from about 1 cm to about 6 cm. In another embodiment of the invention, the electrode comprises an electro-conductive coating.

The plurality of passages 104 from the inner cavity 114 to the outside allows free movement of fluid from the inside to the outside of the cavity. The plurality of passages 104 are positioned on the electrode 102 in areas where the electrode may contact the target tissue. In one embodiment of the invention, the electrode has five to seven passages. In another embodiment, the electrode has less than five passages. In yet another embodiment, the electrode has up 15 passages. The diameter of the passages may range from about 0.010 in. to about 0.020 in. (about 0.25 mm to about 0.5 mm). In some embodiments, the plurality of passages 104 is smaller in size than blood cells. In one embodiment of the invention, the total area of the passages is smaller than the cross-sectional area of the lumen of the flexible tubing.

The pressure sensor 106 may be suspended in the inner cavity 114. Alternatively, the pressure sensor may be mounted inside the inner cavity 114. The pressure sensor 106 measures the pressure of fluid inside the electrode 102. The size of the pressure sensor needs to be minimized so as not to impede fluid flow inside the catheter. This pressure measurement is relayed to the outside. In one embodiment of the invention, this pressure measurement is relayed to the outside via a relay cable. In another embodiment of the invention, this pressure measurement is relayed to the outside wirelessly. In another embodiment of the invention, the pressure measurement may be relayed to a computational device (such as e.g., a personal computer) that also controls the flow of energy into electrode 102.

Shaft 108 may be a tubular shaft and may be made of a corrosion resistant material such as e.g., stainless steel. In some embodiments, shaft 108 is made of a rigid material. Shaft 108 has a distal end and a proximal end. The distal end of shaft 108 is attached to the proximal end of electrode 102 and external to the flexible tubing 110.

Flexible tubing 110 may be of varying length, the length being determined by the application for catheter 100. Flexible tubing 110 is hollow on the inside, thereby creating a lumen 112. In some embodiments, this lumen should have a diameter of at least 0.2 mm, including from about 0.3 to about 1.0 mm.

The flexible tubing may be made from materials suitable for medical use. The flexible tubing may be a flexible durable material (such as e.g., polyethylene), including thermoplastics (such as e.g., nylon) in which braiding is embedded. The flexible tubing may be constructed from a number of different polymers. Exemplary polymers include e.g., polypropylene, oriented polypropylene, polyethylene, crystallized polyethylene terephthalate, polyethylene terephthalate, polyester, and polyvinyl chloride. Alternatively, the flexible tubing may be made from conventional flexible conductively coatable materials, such as e.g., polyurethanes, polyether-block amides, polyolefins, silicone, nylons, polytetrafluoroethylene, polyvinylidene fluoride, fluorinated ethylene propylene polymers, and other conventional materials. The tubing may include radiopaque markers or radiopaque filler such as bismuth or barium sulfate.

In one embodiment of the invention, the flexible tubing is made up from a series of different materials to allow for different material stiffness different sections of the catheter. These sections of different material enable the flexible tubing (and therefore the catheter) to have different mechanical properties such as e.g., flexibility, at different locations along the tubing. Suitable materials to create these different sections include Pebax® resin (AUTOFINA Chemicals, Inc., Philadelphia, Pa.) and other polyether-block co-polyamide polymers.

In one embodiment of the invention, the flexible tubing is used to deliver a cooling fluid such as e.g., saline. This cooling fluid is delivered to the ablation site in order to cool the tip of the catheter so that a larger amount of heart tissue can be destroyed. The rate of flow of the cooling fluid can be varied. The flow rate may range from about 10 mL/min to about 30 mL/min. In one embodiment of the invention, the flow rate may range from about 13 mL/min to about 17 mL/min. In another embodiment, the rate of flow of the cooling fluid is constant (i.e., the cooling fluid is moving at a fixed flow rate).

Another embodiment of the invention is an irrigated ablation catheter that utilizes an electrode, a manifold, and a pressure sensor. Referring to FIG. 2, a side elevational view of catheter 200 is shown. Catheter 200 has flexible tubing 210, electrode 202, manifold 206, pressure sensor 204, and shaft 208. Flexible tubing 210 has a proximal, a distal end, and lumen 212. Manifold 206 is connected to the distal end of flexible tubing 210. Manifold 206 has a lumen 214 inside of which pressure sensor 204 is located (i.e., suspended or mounted). Manifold 206 is connected to electrode 202. Shaft 208 is also connected to manifold 206 external to the flexible tubing. Electrode 202 and manifold 206 have a plurality of passages 216, which connect the inner cavity 218 of electrode 202 and the lumen 214 of manifold 206 to the outside. Fluid tube 210 may be of varying lengths, the length being determined by the application for the catheter 200. Fluid tube 210 can be made of a flexible durable material, including thermoplastics such as nylon, in which a braiding is embedded. The electrode 202 may be a single electrode or multiple electrodes surrounding the distal surface of catheter 200. The electrode 200 may have a length of at least 4 mm alternatively from about 1 cm to about 6 cm. Shaft 208 may be made of a rigid material.

The manifold 206 separates the electrode 202 from the fluid tube 210 of catheter 200. Thus, the manifold 202 insulates the electrode 202 from the remainder of the catheter 200. It also minimizes contact between saline inside the catheter and the electrode. The distal passage 220 oriented along the axis at the tip of the electrode 202 includes an insulative lining 222. The insulative lining 222 insulates the distal passage 220 from the electrode 202. The manifold 206 may be made of a variety of materials that have insulating properties. The manifold may be made from a plastic such as e.g., acetal, polyetheretherketone (PEEK), and high-density polyethylene (HDPE).

In one embodiment of the invention, the electrode 202 does not have an inner cavity. In that embodiment, the plurality of passages 216 directly connects the lumen 214 of manifold 206 to the outside. In another embodiment of the invention, the electrode 202 does not have distal passage 220. In that alternate embodiment, only the manifold 206 has passages 216.

Catheter 200 has a plurality of passages in the manifold and electrode. In one embodiment, there may be five to seven passages. In another embodiment, the manifold and electrode combined have less than five passages. In yet another embodiment, the manifold and electrode have up to 15 passages.

The pressure sensor 106 and pressure senor 204 may be a fiber optic pressure sensor, which relays pressure measurements to the outside via use of a fiber optic cable. Such a fiber optic pressure sensor may be as small as 0.5 mm in width and only a few nanometers long. The fiber optic cable may be as small as 0.17 mm in diameter. The fiber optic pressure sensor may be one of the commercially available sensors such as the FOBPS family of fiber optic pressure sensors by World Precision Instruments. This pressure sensor may be operably linked to the electrode.

An open irrigation catheter according to the instant disclosure can be operated with a fixed flow rate of cooling fluid inside the catheter (a so-called fixed flow condition). Thus, when an open irrigated ablation catheter has contact with tissue, some of the plurality of openings on the distal electrode will be plugged by the tissue. The pressure inside the electrode will increase as a function of the reduced open irrigation area as well as the fixed flow condition.

Figure 3A:
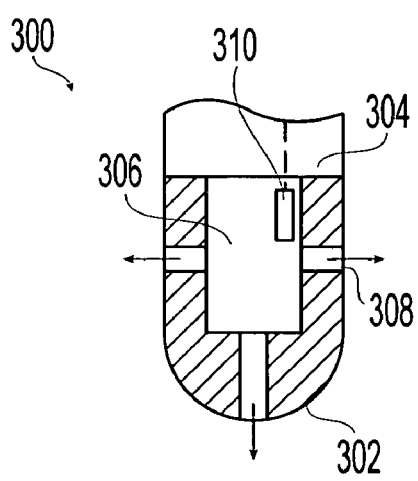
FIG. 3A shows the flow when there is no contacting with the target tissue.
Figure 3B:
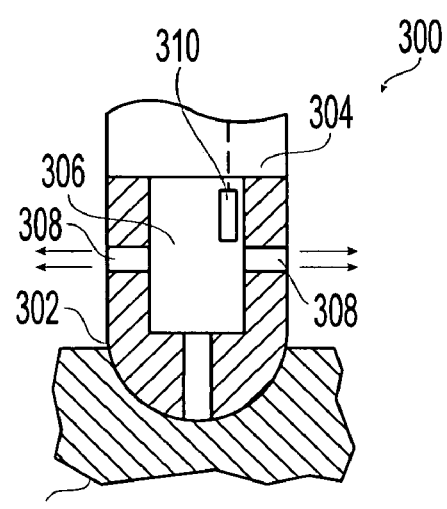
FIG. 3B shows the flow when there is contacting.

FIG. 3 illustrates the flow and pressure change inside the distal end of an irrigated ablation catheter according to one embodiment of the invention. FIG. 3 is a side view of the tip of a catheter at perpendicular orientation. Referring to FIG. 3, only the tip of the catheter 300 is visible. The tip of the catheter has electrode 302 mated to hollow flexible tubing 304. The electrode has a lumen 306 and plurality of passages 308. The plurality of passages 308 connect with the lumen 306 such that fluid can flow into and out of the lumen. Pressure sensor 310 is suspended inside lumen 306. Since the pressure sensor 310 is suspended inside the lumen 306, it measures the pressure inside container created by fluid moving in and out of the container. FIG. 3A shows the fluid and pressure flow in the catheter when there is no contacting with a target tissue, while FIG. 3B shows the fluid and pressure flow in the catheter when there is contacting. In the absence of any contacting (as seen in FIG. 3A), there is a fixed flow of fluid from the inside of the catheter tip to the outside and therefore a constant pressure. When the catheter 300 contacts target tissue 312, one or more of plurality of passages 308 are blocked by the tissue. Thus, the pressure inside the catheter will increase. This increase in pressure is then detected by the pressure sensor. Based on this increase in pressure, an operator of the catheter will then recognize that tissue contact has been made and ablation can proceed. Alternatively, the increase in pressure is operatively linked to the electrode. Thus, upon an increase in pressure, the electrode will be triggered automatically.

FIG. 4 illustrates the flow and pressure change inside the distal end of an irrigated ablation catheter according to one embodiment of the invention based on an axial view of the catheter at horizontal or parallel orientation. In FIG. 4 only electrode 402, plurality of passages 404, lumen 406, and pressure sensor 408 of catheter 400 are visible. The plurality of passages connects the lumen 406 to the outside. When the catheter 400 is not in contact with a tissue (as seen in FIG. 4A), fluid flows from the catheter to the outside at a fixed rate thereby maintaining a constant pressure inside the catheter. When catheter 400 is in contact with target tissue 410 (as seen in FIG. 4B), a number of the plurality of passages 404 become blocked as a result of which the pressure increases inside the catheter. Again, based on this increase in pressure, an operator of the catheter will then recognize that tissue contact has been made and ablation can proceed. Alternatively, the increase in pressure is operatively linked to the electrode so that the electrode is triggered automatically upon an increase in pressure.

FIG. 5 illustrates the flow and pressure change inside the distal end of an irrigated ablation catheter according to one embodiment of the invention based on a side view of the catheter at horizontal or parallel orientation. Only the tip of catheter 500 is shown. Catheter 500 has electrode 502 connected to hollow flexible tubing 504. The electrode 502 has a plurality of openings 506, which connect the lumen 508 with the outside. Inside lumen 508, pressure sensor 510 is suspended. In the non-contacting state (as shown in FIG. 5 A), fluid moves out of the electrode through plurality of openings 506. This flow of fluid is at a constant rate and therefore the pressure inside the catheter is constant. In the contacting state (as shown in FIG. 5 B), one or more of the plurality of openings 506 are blocked due to contact of the electrode 502 with target tissue 512. Because of the contacting, the pressure inside the catheter will increase. This increase in pressure is detected by the pressure sensor and indicates to the operator of the catheter that tissue contact has been made.

While only the distal end (i.e., the tip) of an irrigated catheter is shown in FIGS. 1 and 2, one of skill in the art would understand that a complete catheter set-up has additional elements well known to those of skill in the art. For example, a complete catheter set-up may contain a catheter (with flexible tubing and an electrode), a pressure sensor, an energy source (such as e.g., an RF generator), a pump that supplies the cooling fluid and a proximal end control handle. The length of the catheter may be from about 50 cm to about 150 cm. The diameter of the catheter is within ranges well known in the industry, including, from about 4 to 16 French.

In some embodiments, the source for energy emitted by the electrode of an irrigated ablation catheter according to the instant disclosure is radiofrequency energy, although other sources for energy can be utilized including direct current, laser, ultrasound, and microwave. During the ablation procedure, the radiofrequency energy from the electrode is conducted to the tissue to be ablated. If sufficient energy is conducted to the tissue for a sufficient period of time, a satisfactory ablation lesion is formed. The lesion being formed should have an adequate depth along the entire length of the lesion to avoid gaps.

The energy source may be an RF generator. In one embodiment of the invention, the RF generator may provide up to 150 watts of power at about 500 kHz, and will have capability for both temperature monitoring and impedance monitoring. A suitable generator would be, for example, a Model No. EPT-1000 available from the EP Technologies Division of Boston Scientific Corp. of Natick, Mass. In another embodiment of the invention, the RF generator may provide up to 70 W at 550-kHz of unmodulated sine wave output.

Temperature sensors, such as e.g., thermistors or thermocouples, may be secured to the surface of the catheter to monitor the temperature of the tissue being ablated. Thus, these thermosensing devices determine whether sufficient energy has been applied to the tissue to create an adequate linear lesion. After the ablation procedure is completed, a sensing electrode, such as a tip electrode, may be utilized as a sensing system to determine if the arrhythmia has been eliminated at the particular location within the heart. Additional ablation lesions or tracks can then be produced using the ablation catheter at the same or different locations within the heart.

In one embodiment of the invention, the catheter has multiple individually controllable electrodes on the tip of the catheter that contacts the tissue. Such individually controllable electrodes allow ablation to proceed only in areas where the electrode has made contact with the tissue. This minimizes the amount of heat created at the tip of the electrode and therefore minimizes the amount of coagulum.

In operation, a modified Seldinger technique is normally used for the insertion of the associated dilators, introducers, and ablation catheter into the body. The appropriate vessel is accessed by needle puncture. The soft flexible tip of an appropriately sized guidewire is then inserted through, and a short distance beyond, the needle into the vessel. Firmly holding the guidewire in place, the needle is removed. The guidewire is then advanced through the vessel into the appropriate portion of the heart for the ablation procedure. A preformed, shaped guiding introducer or guiding introducer system, such as those disclosed in U.S. Pat. No. 5,575,766, may be utilized to assist in proper placement of the ablation catheter in the heart. Alternatively, or additionally, the ablation catheter may contain a mechanism to make it steerable, such as a pull wire, so that the ablation catheter may be guided within the vessel or chamber of the human body to be ablated without use of a guiding introducer. The ablation catheter can also be directed to the location to be ablated by other steering mechanism, such as a rail or a guidewire. In the heart, tissue contact is verified based on pressure measurements.

In one embodiment, with a guidewire in place, the dilator is placed over the guidewire with the appropriate guiding introducer, or guiding introducer system. The dilator and the guiding introducer or guiding introducer system generally forms an assembly to be advanced together along the guidewire into the appropriate vessel. After insertion of the assembly, the guidewire is then withdrawn.

The guiding introducer or guiding introducer system for use in the heart is then passed over the guidewire through its lumen and positioned to allow ablation and mapping procedures to be performed at the appropriate location in the heart. Once the guiding introducer or guiding introducer system is in place at the appropriate location within the heart, the ablation catheter is advanced through the lumen of the guiding introducer or guiding introducer system.

After the desired location for ablation is determined, and the ablation catheter has been guided to that location, the electrode of the catheter is at or near the tissue to be ablated. Placement of the portion of the catheter body containing the openings against the tissue to be ablated is achieved by conventional procedures such as fluoroscopy, the use of markers, or other conventional methods. Tissue contact is then verified by detecting an increase of pressure inside the catheter. Energy is subsequently passed through the electrode and ablation proceeds.

Thus, the invention also includes methods of operating an open irrigated ablation catheter with an internal pressure sensor. The operation of an ablation catheter, as previously described in detail, consists of the following general steps. An ablation catheter is first inserted into the patient. An operator maneuvers the distal end (the end of the catheter with the electrode) by manipulating proximal end control handle by any means well known in the art including, but not limited to, pullwires. When the electrode is in the proper location, the operator activates the energy source (such as e.g., an RF generator) to allow ablation to proceed. Proper location is verified by detecting an increase in pressure inside the catheter.

The detection of the change in pressure inside the catheter is based on measuring the pressure inside the catheter at any time before tentative tissue contacting is made and then measuring the pressure after tentative tissue contacting. Tissue contacting arises only if the pressure after tentative tissue contacting is greater than the pressure before tentative tissue contacting.

Thus, in one embodiment of the invention, the method of ablation has the steps of (a) providing an open irrigated ablation catheter with an electrode having a lumen and plurality of passages ways and a pressure sensor inside the lumen of the electrode; (b) inserting the catheter into a patient; (c) measuring the pressure in the catheter inside the patient; (d) contacting a target tissue; (e) determining if contacting of the target tissue has been made by (i) measuring the pressure inside the catheter inside the patient after tentative target tissue contact; and (ii) comparing this pressure with that in step (c), with an increase in the pressure being indicative of tissue contacting; and (f) ablating the target tissue for a period of time and under conditions sufficient to ablate the target tissue. The step of ablating the target tissue is achieved by supplying energy, including RF, to the electrode. The step of inserting may comprise the Seldinger technique as well as the other techniques described. The step of inserting includes both the inserting of the catheter and guiding the catheter to the target tissue.

Pharmacological treatments may also be used in combination with ablation procedures to relieve the atrial arrhythmia.

Although various embodiments of this invention have been described above with a certain degree of particularity, those skilled in the art could make numerous alterations to the disclosed embodiments without departing from the spirit or scope of this invention. For example, any means of measuring pressure could be used. All directional references (e.g., upper, lower, upward, downward, left, right, leftward, rightward, top, bottom, above below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed:

1. An ablation catheter comprising:
   (a) an elongated tubing having a distal end, a proximal end, and a lumen;
   (b) an electrode having an inner cavity, a plurality of passages from the inner cavity to an outer surface of the electrode, a distal end and a proximal end;
   (c) a shaft having a distal end and a proximal end, said distal end attached to the proximal end of electrode, the shaft being external to the tubing; and
   (d) a pressure sensor mounted inside the inner cavity of the electrode for sensing pressure change due to a change in fluid flow exiting through at least one of the passages.

2. The ablation catheter of claim 1, wherein said electrode comprises Pt, Ir, gold, a noble metal, or stainless steel.

3. The ablation catheter of claim 2, wherein said electrode comprises a Pt and Ir alloy.

4. The ablation catheter of claim 1, wherein the pressure sensor is a fiber optic pressure sensor.

5. The ablation catheter of claim 4, further comprising a fiber optic cable connected to the fiber optic pressure sensor.

6. The ablation catheter of claim 1, wherein the total area of the passages is smaller than the cross-sectional area of the lumen of the tubing.

7. The ablation catheter of claim 1, wherein the shaft is tubular.

8. The ablation catheter of claim 1, wherein the tubing comprises radiopaque markers or radiopaque filler.

9. The ablation catheter of claim 1, wherein the electrode emits radiofrequency energy.

10. An ablation catheter comprising:
(a) an elongated tubing having a distal end, a proximal end, and a lumen;
(b) a manifold having a distal end, a proximal end, a lumen, at least one passage from the lumen to an outer surface of the manifold;
(c) an electrode having an inner cavity, at least one passage from the inner cavity to an outer surface of the electrode, a distal end and a proximal end;
(d) a shaft having a distal end and a proximal end, said distal end attached to the proximal end of the manifold and external to the tubing; and
(e) a pressure sensor mounted inside the inner cavity of the electrode for sensing pressure change due to a change in fluid flow exiting through the passage from the inner cavity to the outer surface of the electrode,
wherein said manifold is attached to the proximal end of the tubing such that the lumen of the manifold and the lumen of the tubing are connected,
and wherein said electrode is attached to the proximal end of the manifold such that the lumen of the manifold is mated to the inner cavity of the electrode.

11. The ablation catheter of claim 10, wherein said electrode comprises Pt, Ir, gold, a noble metal, or stainless steel.

12. The ablation catheter of claim 11, wherein said electrode comprises a Pt and Ir alloy.

13. The ablation catheter of claim 10, wherein the pressure sensor is a fiber optic pressure sensor.

14. The ablation catheter of claim 13, further comprising a fiber optic cable connected to the fiber optic pressure sensor.

15. The ablation catheter of claim 10, wherein the total area of the passages is smaller than the cross-sectional area of the lumen of the tubing.

16. The ablation catheter of claim 10, wherein the shaft is tubular.

17. The ablation catheter of claim 10, wherein the tubing comprises radiopaque markers or radiopaque filler.

18. The ablation catheter of claim 10, wherein the electrode emits radiofrequency energy.

19. The ablation catheter of claim 10, the manifold comprises of a thermally insulative material.

20. A method of ablation comprising:
(a) providing an open irrigated ablation catheter comprising an electrode having a lumen and plurality of passages and a pressure sensor inside the lumen of the electrode for sensing pressure change due to a change in fluid flow exiting through at least one of the passages;
(b) inserting the catheter into a patient;
(c) measuring the pressure in the catheter inside the patient;
(d) contacting a target tissue,
(e) determining if contacting of the target tissue has been made by
(i) measuring the pressure inside the catheter inside the patient after tentative target tissue contact; and
(ii) comparing this pressure with that in step (c), wherein an increase in the pressure is indicative of tissue contact due to change in fluid flow exiting through at least one of the passages; and
(f) ablating the target tissue if there is contact.

21. The method of claim 20, wherein the electrode of the catheter comprises Pt, Ir or alloy thereof.

22. The method of claim 20, wherein the pressure sensor of the electrode is a fiber optic pressure sensor.

23. The method of claim 20, wherein the step of ablating comprises supplying radiofrequency energy to the electrode.

24. The method of claim 20, wherein a cooling fluid is passed through the catheter.

25. The method of claim 24, wherein the cooling fluid is saline.

26. An ablation catheter comprising:
(a) an elongated tubing having a distal end, a proximal end, and a lumen;
(b) a shaft having a distal end, a proximal end, and a lumen, the shaft being external to the elongated tubing;
(c) a distal member coupled to the distal end of the shaft to form an interior space of the catheter, the distal member having at least one passage fluidicly coupled between the interior space of the catheter and the outer surface of the distal member, the interior space of the catheter being fluidicly coupled to the lumen of the elongated tubing, the distal member including an electrode; and
(d) a pressure sensor disposed inside the interior space of the catheter for sensing pressure change due to a change in fluid flow exiting through the passage.

27. The ablation catheter of claim 26, wherein the electrode includes at least one passage fluidicly coupled between the interior space of the catheter and the outer surface of the distal member.

28. The ablation catheter of claim 26, wherein the distal member includes a manifold having a proximal end connected to the distal end of the shaft and a distal end connected to the electrode.

29. The ablation catheter of claim 28, wherein the manifold includes at least one passage fluidicly coupled between the interior space of the catheter and the outer surface of the distal member.

30. The ablation catheter of claim 28, wherein the manifold comprises a thermally insulative material.

31. The ablation catheter of claim 28, wherein the electrode includes at least one passage fluidicly coupled between the interior space of the catheter and the outer surface of the distal member, and wherein the manifold includes at least one passage fluidicly coupled between the interior space of the catheter and the outer surface of the distal member.

32. The ablation catheter of claim 26, wherein the distal member includes an inner cavity forming a portion of the interior space of the catheter, and wherein the pressure sensor is disposed inside the inner cavity of the distal member.

* * * * *